United States Patent [19]
Fleming

[11] 4,112,103
[45] Sep. 5, 1978

[54] ANTIARRHYTHMIC
(+,−)-CIS-α-[3-(2,6-DIMETHYL-1-PIPERIDINYL)PROPYL]-α-PHENYL-2-PYRIDINEMETHANOLS

[75] Inventor: Robert Willerton Fleming, Ann Arbor, Mich.

[73] Assignee: Parke, Davis & Company, Detroit, Mich.

[21] Appl. No.: 772,203

[22] Filed: Feb. 25, 1977

Related U.S. Application Data

[63] Continuation-in-part of Ser. No. 676,964, Apr. 15, 1976, abandoned.

[51] Int. Cl.² ............................................. C07D 213/38
[52] U.S. Cl. ............................... 424/267; 260/293.51; 260/293.69; 260/293.8; 260/293.9
[58] Field of Search ..................... 260/293.69; 424/267

[56] References Cited
U.S. PATENT DOCUMENTS 2,712,022  6/1955  Adamson ......................... 260/293.69

OTHER PUBLICATIONS

Peterson, D. *J. Am. Chem. Soc.*, 93(16), 4027–4031 (1971).

*Primary Examiner*—Henry R. Jiles
*Assistant Examiner*—Richard A. Schwartz
*Attorney, Agent, or Firm*—Stephen Raines; David B. Ehrlinger; Frank S. Chow

[57] ABSTRACT (+,−)-cis-α[3-(2,6-Dimethyl-1-piperidinyl)propyl]-α-phenyl-2-pyridinemethanol and acid-addition salts. The compounds are pharmacological agents, especially antiarrhythmic agents. The compounds can be produced by reacting pyridyllithium with cis-γ-(2,6-dimethylpiperidino)butyrophenone, or by reacting cis-1-(3-lithiopropyl)-2,6-dimethylpiperidine with 2-benzoylpyridine. Pharmaceutical compositions comprising (+,−)-cis-α-[3-(2,6-dimethyl-1-piperidinyl)propyl]-α-phenyl-2-pyridinemethanol and acid-addition salts thereof and methods for treating cardiac arrhythmia using said pharmaceutical compositions are also disclosed.

7 Claims, No Drawings

ANTIARRHYTHMIC (+,−)-CIS-α-[3-(2,6-DIMETHYL-1-PIPERIDINYL)-PROPYL]-α-PHENYL-2-PYRIDINEMETHANOLS

CROSS-REFERENCE TO RELATED APPLICATIONS

This is a continuation-in-part of copending application, Ser. No. 676,964, filed Apr. 15, 1976 now abandoned.

SUMMARY AND DETAILED DESCRIPTION

The present invention relates to new 1-piperidinebutanol compounds and methods for their preparation. More particularly, the invention relates to (+,−)-cis-α-[3-(2,6-dimethyl-1-piperidinyl)propyl]-α-phenyl-2-pyridinemethanol which has the formula

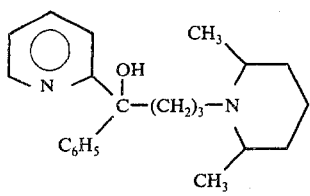   I to acid-addition salts thereof, methods for the production of the foregoing compounds, pharmaceutical compositions containing said compounds and methods for treating cardiac arrhythmia using said compounds.

In accordance with the invention, the foregoing compounds can be produced by reacting a compound of the formula

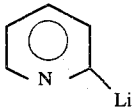   II with a compound of the formula

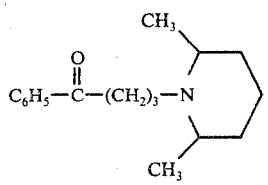   III having a cis configuration.

This reaction is generally carried out in a solvent such as an ether (diethyl ether, tetrahydrofuran, diethylene glycol dimethyl ether, etc.), a hydrocarbon (benzene, toluene, hexane, heptane, etc.), or mixtures thereof for periods of from 1 to 12 hours at from −80° C. to +10° C., preferably 1 to 2 hours at −60° C. to −80° C. followed by 1 to 3 hours at from −5° C. to +5° C. The preferred solvent system employs tetrahydrofuran, optionally mixed with heptane.

While at least 1 mole of pyridyllithium (II) should be used for each mole of piperidine compound (III), an excess of the lithium compound is preferred.

The intermediate metallic derivative of a compound of formula I is hydrolyzed under acidic (dilute aqueous hydrochloric acid, aqueous ammonium chloride, dilute aqueous sulfuric acid, etc.), neutral or basic (dilute aqueous sodium hydroxide, dilute aqueous potassium hydroxide, etc.) conditions, preferably neutral conditions.

The product may be isolated as the free base or an acid-addition salt thereof by suitable adjustment of the pH.

The cis-γ-(2,6-dimethylpiperidino)butyrophenone is prepared by reacting an excess of cis-2,6-dimethylpiperidine with γ-chlorobutyrophenone, ethylene ketal in the presence of sodium iodide at reflux for about 48 hours, followed by hydrolysis of the resulting amino ketal with aqueous hydrochloric acid and then basification with aqueous sodium hydroxide.

The γ-chlorobutyrophenone, ethylene ketal is prepared by reacting γ-chlorobutyrophenone with ethylene glycol using p-toluenesulfonic acid as a catalyst. The reaction is carried out utilizing benzene as a solvent and a water trap coupled into the reaction system. The reaction mixture is refluxed until the desired amount of water is collected, followed by neutralization of the acid and removal of the solvent.

Also, in accordance with the invention, the compounds of the invention can be prepared by reacting a compound of the formula

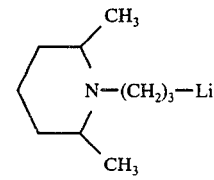   IV having a cis configuration with 2-benzoylpyridine in a suitable solvent such as an ether (diethyl ether, tetrahydrofuran, diethylene glycol dimethyl ether, etc.) for from 4 to 24 hours at 0° C. to 60° C. The preferred reaction conditions employ tetrahydrofuran as the solvent and a reaction time of from 12 to 18 hours at a temperature range of from 20° C. to 35° C.

It is preferred to use approximately equivalent amounts of the lithium derivative of structure IV and 2-benzoylpyridine.

The intermediate metallic derivative of a compound of formula I is hydrolyzed under acidic (dilute aqueous hydrochloric acid, aqueous ammonium chloride, dilute aqueous sulfuric acid, etc.), neutral or basic (dilute aqueous sodium hydroxide, dilute aqueous potassium hydroxide, etc.) conditions, preferably neutral conditions.

The product may be isolated as the free base or an acid-addition salt thereof by suitable adjustment of the pH.

The cis-1-(3-lithiopropyl)-2,6-dimethylpiperidine is prepared by reacting one equivalent of cis-1-(3-chloropropyl)-2,6-dimethylpiperidine with two equivalents of lithium over a 6-hour period in tetrahydrofuran. After filtration, the remaining solution is reacted directly with 2-benzoyl pyridine.

The cis-1-(3-chloropropyl)-2,6-dimethylpiperidine is prepared by reacting thionyl chloride with cis-2,6-dimethyl-1-piperidinepropanol in benzene at a temperature of from 0° C. to 5° C. for 30 minutes followed by 2 hours at reflux. The chlorinated product is isolated as the hydrochloride by filtration.

The cis-2,6-dimethyl-1-piperidinepropanol is prepared by reacting 3-bromopropanol with an excess of cis-2,6-dimethylpiperidine in refluxing xylene for a period of about 2 hours. The cis-2,6-dimethyl-1-piperidinepropanol is separated by distillation.

The free base of formula I forms acid-addition salts, which are also part of this invention, with any of variety of inorganic and organic acids. Typical acid-addition salts are formed with such acids as hydrochloric, hydrobromic, sulfuric, sulfamic, nitric, phosphoric, acetic, citric, tartaric, succinic, oxalic, benzoic, maleic, malic, lactic, gluconic, naphthalene-1,5-disulfonic, methanesulfonic, p-toluenesulfonic, and pamoic acids. The free bases and their salt forms are interconvertible by adjustment of the pH. They differ in solubility properties but are otherwise equivalent for the purposes of the invention.

The compounds of the invention can exist in anhydrous form as well as in solvated, including hydrated, forms. In general, the hydrated forms and the solvated forms with pharmaceutically acceptable solvents are equivalent to the anhydrous or unsolvated form for the purposes of the invention. The compounds of the inventions may also be obtained as R and S isomers by standard resolution techniques.

The compounds of the invention are new chemical compounds of value as pharmacological agents. More specifically, these compounds are antiarrhythmic agents. The activity of these compounds is shown by way of the following antiarrhythmic screen.

Dogs were operated on according to the procedure reported in Circulation 1, 1318 (1950). (+,−)-cis-α-[3-(2,6-Dimethyl-1-piperidinyl)propyl]-α-phenyl-2-pyridinemethanol, lidocaine and quinidine were tested intravenously 19 to 24 hours after coronary artery ligation. The degree of effectiveness of the compound was determined by the degree of conversion of ventricular ectopic beats to sinus beats. The table shown below gives the results of the screen performed on (+,−)-cis-α-[3-2,6-dimethyl-1-piperidinyl)propyl]-α-phenyl-2-pyridinemethanol and the known antiarrhythmic agents, lidocaine and quinidine.

TABLE

| Compound | Dose* | Time Post Dose | % Conversion |
|---|---|---|---|
| Lidocaine | 10 mg/kg i.v. | 5 min. | 92 |
| | | 20 min. | 0 |
| | | 55 min. | 0 |
| Quinidine | 20 mg/kg i.v. | 5 min. | 66 |
| | | 20 min. | 35 |
| | | 55 min. | 41 |
| (+,−)-cis-α-[3-(2,6-dimethyl-1-piperidinyl)propyl]-α-phenyl-2-pyridinemethanol | 5 mg/kg i.v. | 2 min. | 91 |
| | | 20 min. | 76 |
| | | 55 min. | 66 |

*Dose calculated as free base, tested as salts.

In addition the present invention relates to pharmaceutical compositions and methods employing (+,−)-cis-α-[3-(2,6-dimethyl-1-piperidinyl)propyl]-α-phenyl-2pyridinemethanol and pharmaceutically acceptable acid-addition salts thereof. Some typical examples of pharmaceutically acceptable acid-addition salt forms are the hydrochloride, sulfate, phosphate, citrate, pamoate, acetate and maleate salts.

More particularly, (+,−)-cis-α-[3-(2,6-dimethyl-1-piperidinyl)propyl]-α-phenyl-2-pyridinemethanol and pharmaceutically acceptable acid-addition salts thereof are highly useful in controlling cardiac arrhythmias in mammals, such as cats, dogs, horses, human beings, etc., when administered in amounts ranging from about 0.1 to about 10 mg. per kg. of body weight per day, and such dosage units are employed that a total of from about 7 to about 700 mg. of active ingredient for a subject of about 70 kg. body weight are administered in a 24 hour period, preferably in divided doses. A preferred dosage regimen employs a range of from 1 to 5 mg. of active ingredient per kg. of body weight per day and wherein the total daily dosage is divided into four units and each taken after an appropriate time interval.

The compounds of the present invention may be administered by any convenient route such as orally, intraperitoneally, subcutaneously, intramuscularly or intravenously.

Compositions according to the present invention having the desired clarity, stability, and adaptability for parenteral use are obtained by dissolving from 0.10 to 10.0% by weight of active compound in a vehicle such as water, a polyhydric aliphatic alcohol or mixtures thereof. In addition to water, especially satisfactory are glycerin, propylene glycol, and the polyethylene glycols. The polyethylene glycols consist of a mixture of non-volatile, normally liquid, polyethylene glycols which are soluble in both water and organic liquids and which have molecular weights of from about 200 to about 1500. Although the amount of active compound dissolved in the above vehicle may vary from 0.10 to 20.0%. by weight, it is preferred that the amount of active compound employed be from about 1.0% to about 10.0% by weight. Although various mixtures of the aforementioned non-volatile polyethylene glycols may be employed, it is preferred to use a mixture having an average molecular weight of from about 200 to about 400.

In addition to the active compounds, the parenteral solutions of the present invention may also contain various preservatives which may be used to prevent bacterial and fungal contamination. The preservatives which may be used for such purpose are, for example, benzyl alcohol, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter is is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

The preferred concentration of active compound is 1 to 50 mg./ml. of the finished compositions when intramuscular injection is the purpose for which the compositions are intended. They are equally adapted to intravenous administration when diluted with water or diluents employed in intravenous therapy such as isotonic glucose in appropriate quantities. For this use, initial concentrations down to about 0.5 to 25 mg./ml. of active compound are satisfactory. They are also adapted to oral administration when diluted with drinking water.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions syrups, wafers, chewing gum, and the like. Such compositions and preparations should contain at least 0.1% of active compound. The percentage in the compositions and preparations may, of course, be varied and may conveniently be between about 5 to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 1 and 200 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as perservatives, a dye and a flavoring such as cherry or orange flavor. Of course, any material used in preparing any dosage unit form should be pharmaceutically pure and substantially nontoxic in the amounts employed.

The invention is illustrated by the following examples:

EXAMPLE 1

At $-78°$ C. 180 ml. of a 1.6M solution of butyl lithium in heptane is added with stirring to 200 ml. of tetrahydrofuran. The mixture is stirred under nitrogen while a solution of 43 g. of 2-bromopyridine in 50 ml. of tetrahydrofuran is added slowly while maintaining the temperature below $-65°$ C. After stirring for 1 hour, the mixture is treated with a solution of 65 g. of cis-$\alpha$-(2,6-dimethylpiperidino)butyrophenone in 70 ml. of tetrahydrofuran over a period of 10 minutes and stirred at $-65°$ to $-75°$ C. for one additional hour. The mixture is stirred and allowed to warm to $0°$ C. over a period of 2 hours, then treated with 30 ml. of water. The supernatant organic layer is decanted from the precipitated solid and evaporated at reduced pressure to about one-third its previous volume. The residue is poured into 2.5 l. of cold dilute aqueous sodium hydroxide. The resulting precipitate of (+,−)-cis-$\alpha$-[3-(2,6-dimethyl-1-piperidinyl)propyl]-$\alpha$-phenyl-2-pyridinemethanol is removed by filtration, washed with water and dried; m.p. $70°-71°$ C. after crystallization from petroleum ether.

If the product is recrystallized from aqueous methanol, a monohydrate results; m.p. $101°-102°$ C.

The monohydrochloride salt is prepared by dissolving the anhydrous free base in 2-propanol and adding an equivalent amount of a 10% solution of dry hydrogen chloride in 2-propanol, followed by dilution with ether and filtration of the precipitated salt; m.p. $171°-172°$ C.

Intermediates (a) cis-$\gamma$-(2,6Dimethylpiperidono)butyrophenone

A mixture of 619 g. of $\gamma$-chlorobutyrophenone, ethylene ketal, 700 g. of cis-2,6-dimethylpiperidine and 16 g. of sodium iodide is stirred and heated at reflux for 48 hours. The mixture is cooled, diluted with 1 l. of anhydrous ether and filtered to remove cis-2,6-dimethylpiperidine hydrochloride. The filter cake is washed with 1 l. of ether and the filtrate and washings combined. The resulting ether solution is washed five times with 500 ml. portions of water, then extracted with a solution of 300 ml. of concentrated hydrochloric acid in 3 l. of water. The acid extract is washed with 500 ml. of ether, then heated to $70°-80°$ and allowed to cool to room temperature over a period of 16 hours. The resulting solution is basified with 50% aqueous sodium hydroxide and the organic layer is separated. The aqueous layer is extracted with 500 ml. of ether and the extract is combined with the organic layer. The combined extract is washed several times with water, dried and evaporated. The oily residue is distilled at reduced pressure to give cis-$\alpha$-(2,6-dimethylpiperidino)butyrophenone; b.p. $138°-141°$ C./0.1 mm.

(b) $\gamma$-Chlorobutyrophenone, Ethylene Ketal

A mixture of 500 g. of $\gamma$-chlorobutyrophenone, 225 g. of ethylene glycol, 10 g. of p-toluenesulfonic acid and 1.5 l. of benzene is heated at reflux under a water separator until water collection ceases. The resulting solution is cooled, neutralized with 10 ml. of triethylamine and evaporated at reduced pressure to give $\gamma$-chlorobutyrophenone, ethylene ketal, suitable for use without further purification. (The pure material boils at $100°-118°$ C./0.1–0.8 mm. and melts at $57°-59°$ C.)

EXAMPLE 2

A solution of 18.9 g. of cis-1-(3-chloropropyl)-2,6-dimethylpiperidine in 50 ml. of tetrahydrofuran is added dropwise under a nitrogen atmosphere to a stirred mixture of 1.4 g. of lithium wire and 50 ml. of tetrahydrofuran over a period of 2 hours. After the addition is complete, the mixture is stirred another 4 hours under nitrogen, the excess lithium metal removed manually and a solution of 18.3 g. of 2-benzoylpyridine in 100 ml. of tetrahydrofuran is added dropwise with stirring over a period of 2 hours. The mixture is stirred for 16 hours, then treated with 5 ml. of water. The organic phase is decanted from the precipitated solid and evaporated at reduced pressure to about one-fourth its previous volume. This solution is poured into 400 ml. of water, the solution is acidified with acetic acid and washed with ether. The aqueous acid solution is basified with aqueous sodium hydroxide and extracted with ether. The ether extract is washed with water, dried and evaporated to give (+,−)-cis-$\alpha$-[3-(2,6-dimethyl-1-piperidinyl)propyl]-$\alpha$-phenyl-2-pyridinemethanol; m.p. (monohydrate) $100°-102°$ C. after crystallization from aqueous methanol.

Intermediates (a) cis-1-(3-Chloropropyl)-2,6-dimethylpiperidine

A stirred solution of 171 g. of cis-2,6-dimethyl-1-piperidinepropanol in 400 ml. of benzene is cooled to $0°-5°$ and 143 g. of thionyl chloride is added dropwise over a period of 30 minutes. The mixture is then heated at reflux for 2 hours, cooled and diluted with 1 l. of ether. The resulting precipitate of cis-1-(3-chloropropyl)-2,6-dimethylpiperidine hydrochloride is collected by filtration; m.p. $173°-174°$ C. after crystallization from 2-propanol-ether. The free base is prepared as needed by dissolving the hydrochloride in a minimum amount of water, cooling and adding a slight excess of 50% aqueous sodium hydroxide. The liberated base is immediately extracted with several portions of benzene.

The extracts are combined, dried and evaporated to give the free base, cis-1-(3-chloropropyl)-2,6-dimethylpiperidine.

(b) cis-2,6-Dimethyl-1-piperidinepropanol

A stirred solution of 460 g. of cis-2,6-dimethylpiperidine in 300 ml. of xylene is treated with 278 g. of 3-bromopropanol over a period of 15 minutes. The mixture is stirred and heated at reflux for 2 hours, then allowed to cool while stirring for 16 hours. The mixture is filtered and the filtrate evaporated at reduced pressure. The residue is distilled at reduced pressure to give cis2,6-dimethyl-1-piperidinepropanol; b.p. 147°–149° C./25 mm.

EXAMPLE 3

Preparation of capsule formulation

| Ingredient | Milligrams per Capsule |
| --- | --- |
| (+,−)-cis-α-[3-(2,6-dimethyl-1-piperidinyl)propyl]-α-phenyl-2-pyridinemethanol hydrochloride | 200 |
| Starch | 80 |
| Magnesium stearate | 5 |

The active ingredient, starch and magnesium stearate are blended together. The mixture is used to fill hard shell capsules of a suitable size at a fill weight of 285 milligrams per capsule.

I claim:

1. (+,−)-cis-α-[3-(2,6-Dimethyl-1-piperidinyl)propyl]-α-phenyl-2-pyridinemethanol and acid-addition salts thereof.

2. The compound of claim 1 having the name (+,−)-cis-α-[3-(2,6-dimethyl-1-piperidinyl)propyl]-α-phenyl-2-pyridinemethanol hydrochloride.

3. An antiarrhythmic composition in dosage unit form, comprising a pharmaceutical carrier and an effective antiarrhythmic amount of a compound of claim 1 wherein said acid-addition salts are pharmaceutically acceptable acid-addition salts.

4. The antiarrhythmic composition of claim 3 having between 1 and 200 mg. of active ingredient per dosage unit.

5. A method for controlling cardiac arrhythmia which comprises administering a compound of claim 1 wherein said acid-addition salts are pharmaceutically acceptable acid-addition salts to a mammal in a dose of from about 0.1 to about 10 mg. per kg. of body weight per day.

6. The method of claim 5 wherein said total dose is administered in from two to six equal portions evenly spaced over a 24 hour period.

7. The method of claim 5 wherein the dose range is from 1 to 5 mg. per kg. of body weight per day.

* * * * *